United States Patent
Gradel et al.

(10) Patent No.: US 7,455,684 B2
(45) Date of Patent: Nov. 25, 2008

(54) DEVICE COMPRISING ANTERIOR PLATE FOR VERTEBRAL COLUMN SUPPORT

(75) Inventors: Thomas Gradel, Ayze (FR); Jean-Philippe Lemaire, Saulon la Chapelle (FR)

(73) Assignee: Vitatech, Marignier (FR)

( * ) Notice: Subject to any disclaimer, the term of this patent is extended or adjusted under 35 U.S.C. 154(b) by 61 days.

(21) Appl. No.: 10/539,161

(22) PCT Filed: Dec. 16, 2003

(86) PCT No.: PCT/FR03/03735

§ 371 (c)(1), (2), (4) Date: Jun. 14, 2005

(87) PCT Pub. No.: WO2004/064654

PCT Pub. Date: Aug. 5, 2004

(65) Prior Publication Data

US 2006/0116676 A1    Jun. 1, 2006

(30) Foreign Application Priority Data

Dec. 17, 2002    (FR) .................... 02 16235

(51) Int. Cl.
*A61B 17/70* (2006.01)
(52) U.S. Cl. ...................... 606/246; 606/278
(58) Field of Classification Search .......... 606/61, 606/72, 73, 246, 250–253, 278
See application file for complete search history.

(56) References Cited

U.S. PATENT DOCUMENTS

| | | | |
|---|---|---|---|
| 4,648,388 A | | 3/1987 | Steffee |
| 5,368,594 A | * | 11/1994 | Martin et al. ............. 606/61 |
| 5,584,831 A | * | 12/1996 | McKay ..................... 606/61 |
| 5,662,652 A | * | 9/1997 | Schafer et al. ............ 606/61 |
| 5,713,898 A | | 2/1998 | Stucker |
| 6,136,002 A | * | 10/2000 | Shih et al. ................. 606/61 |
| 6,187,005 B1 | * | 2/2001 | Brace et al. ............... 606/61 |
| 6,206,879 B1 | * | 3/2001 | Marnay et al. ............ 606/53 |
| 2002/0068940 A1 | | 6/2002 | Gaines |
| 2004/0092929 A1 | * | 5/2004 | Zindrick ................... 606/61 |

(Continued)

FOREIGN PATENT DOCUMENTS

DE    9314297 U1    5/1994

(Continued)

*Primary Examiner*—Eduardo C. Robert
*Assistant Examiner*—Nicholas Woodall
(74) *Attorney, Agent, or Firm*—William H. Eilberg

(57) ABSTRACT

In a device including an anterior plate for vertebral column support, there is at least one connecting sliding piece which is used to connect an anchoring screw to a securing rod. The securing rod is inserted into a cylindrical bearing and is fixed using a tightening device including a small clamp and a tightening screw. The connecting sliding piece includes at least one tip which extends away from the cylindrical bearing for the securing rod, in a direction which converges with the axis of the anchoring screw. In this way, the connecting sliding piece is provisionally fixed by pressing same against a vertebra, the anchoring screw is subsequently screwed in place and, finally, the securing rod is inserted laterally into the cylindrical bearing before being tightened using the small clamp and the tightening screw. The device is designed for anterior implantation on a vertebral column.

4 Claims, 3 Drawing Sheets

U.S. PATENT DOCUMENTS

2004/0147929 A1* 7/2004 Biedermann et al. .......... 606/61
2004/0162558 A1* 8/2004 Hegde et al. ................. 606/61
2005/0010216 A1* 1/2005 Gradel et al. ................. 606/61
2005/0277920 A1* 12/2005 Slivka et al. ................. 606/61

FOREIGN PATENT DOCUMENTS

| EP | 0726064 A2 | 8/1996 |
| EP | 1093763 A2 | 4/2001 |
| WO | WP 91/11967 | 8/1991 |

* cited by examiner

DEVICE COMPRISING ANTERIOR PLATE FOR VERTEBRAL COLUMN SUPPORT

TECHNICAL FIELD OF THE INVENTION

The subject matter of the present invention is a device for supporting vertebrae in a required position. A device of this kind is used to treat a vertebral column having an abnormal deviation of degenerative or traumatic origin.

Vertebral arthroses or fractures can be treated, for example, and vertebral column deviations such as scoliosis, lordosis and cyphosis corrected.

The document U.S. Pat. No. 4,648,388 discloses a device for treatment of the vertebral column comprising elements anchored in the vertebrae, a fastening rod of circular section and having a smooth exterior surface, and connecting sliding pieces for connecting the anchoring members to the fastening rod. The anchoring members are screws having three main portions: a first end portion with a helicoidal thread adapted to penetrate and to be retained in bone, a smooth cylindrical intermediate portion of smaller diameter, and a second end portion with a helicoidal thread adapted to have a clamping nut screwed onto it. The connecting sliding pieces have a clamping portion conformed to surround a portion of the fastening rod and a connecting portion projecting laterally and pierced by two holes in corresponding relationship that are adapted to have the anchoring screw passed through them. The anchoring screw is first screwed into the bone, the connecting sliding piece is then fitted over the cylindrical intermediate portion of the anchoring screw, and finally the clamping nut is screwed onto the second threaded portion of the tightening screw to press the connecting sliding piece against a vertebra and at the same time to clamp the connecting sliding piece around the fastening rod.

A device of the above kind is intended to support the vertebral column with an appropriate curvature. However, it is found that the mechanical support provided by this device is insufficient. In particular, the direct bearing engagement of the sliding piece on a vertebra excludes all possibility of effective clamping, because of the low mechanical strength of the vertebra in compression, with the result that there is a major risk of the sliding piece sliding and turning on the fastening rod. Also, this device is designed to be fitted to the posterior face of the vertebral column, and is not suited to anterolateral implantation on the lateral portion of the vertebrae. Moreover, once the sliding piece is in position on the screw, it is no longer possible to engage the fastening rod laterally in the sliding piece.

The document WO 91 11967 discloses a device for treatment of the vertebral column from the posterior side comprising double-threaded pedicular screws with an intermediate stop plate to which is attached a sliding piece conformed to receive and retain a fastening rod. The sliding piece includes a lower groove in which the stop plate engages to prevent it rotating relative to the screw and an upper groove in which the fastening rod engages. The threaded portion of the screw passes through the sliding piece and a locking nut with a frustoconical lower bearing surface is screwed onto the threaded portion and forces the fastening rod laterally into the upper groove of the sliding piece to immobilize it. The conical bearing surface of the nut bearing on the cylindrical shape of the fastening rod does not ensure sufficiently rigid fastening of the fastening rod. Moreover, once the sliding piece is fixed to the screw by the nut it is no longer possible to engage the fastening rod laterally.

The document EP 1 093 763 A discloses a device for supporting the vertebral column conforming to the preamble of claim 1. In that document, the sliding piece has four lower edges that are all laterally spaced from the area receiving the connecting rod, which is in the median portion of the sliding piece. This kind of arrangement means that the connecting rod cannot be offset toward the rear of the vertebral column. As a result of this it is relatively difficult to fit it anterolaterally and it is insufficiently stable in the vertebrae when high mechanical forces are applied between successive vertebrae.

The document U.S. Pat. No. 5,713,898 A discloses a device for supporting the vertebral column including two bone screws adapted to be engaged in two opposite holes and including four points close to the screws and a central area for receiving a transverse rod offset relative to the points. It is not possible to offset the connecting rod described in that document toward the rear of the vertebral column either.

The documents US 2002/0068940 and DE 93 14 297 U describe other structures for a device for supporting the vertebral column including two bone screws for two connecting rods. Their structures do not allow the connecting rods to be offset toward the rear of the vertebral column.

SUMMARY OF THE INVENTION

The problem addressed by the present invention is that of designing a new structure for a device for treatment of the vertebral column using a smooth fastening rod and connecting sliding pieces for anchoring members that achieves significantly more effective fastening of the vertebrae, facilitates fitting and adjusting the position of the members relative to each other in three dimensions, and is also suited to fitting anterolaterally. One particular aim is to allow the fastening rod to be offered up and withdrawn by lateral displacement on a sliding piece already in position on a screw or other anchoring member to facilitate fixing the sliding piece to a vertebra, at the same time as improving its stability and to increase its capacity to absorb mechanical forces between successive vertebrae.

To this end, the device of the invention for vertebral column support comprises at least one connecting sliding piece for connecting an anchoring screw to a fastening rod, the structure of the connecting sliding piece being elongate in a general lengthwise direction, the connecting sliding piece comprising a first hole conformed for the passage and fixing of the anchoring screw and receiving means adapted to receive a portion of the fastening rod oriented along a transverse axis perpendicular to the lengthwise direction and to receive clamping means for selectively clamping the fastening rod in said receiving means or releasing it therefrom; the connecting sliding piece comprises two points conformed to penetrate into the bone of a vertebra to retain the connecting sliding piece on the vertebra; the two points are disposed in the region of the sliding piece including the receiving means, on the interior face of the sliding piece and opposite the receiving means, which are on the exterior face of the connecting sliding piece; the two points are parallel to and offset from each other in the direction of the transverse axis of the connecting sliding piece, parallel to the fastening rod; the fastening rod is engaged in the end of the receiving means opposite the anchoring screw in the general lengthwise direction.

The two points in the vicinity of one end of the sliding piece and the anchoring screw engaged in the vicinity of the opposite end of the sliding piece provide stable fixing at three points in a triangular arrangement, which increases the stability of the device when fitted anterolaterally to the vertebral column, and allows positioning of the fastening rod closer to the rear of the vertebral column. At the same time, access to the tightening screws is facilitated.

In one practical embodiment, each point is a generally triangular flat structure in a plane perpendicular to the direction of the transverse axis. Each point advantageously comprises retaining teeth on the two sides of the triangle.

The interior face of the sliding piece adapted to bear against the vertebra is preferably concave and substantially cylindrical with a circular profile. This promotes stability of the sliding piece on the vertebra.

To improve the retention of the sliding piece on the vertebra, each point extends in a substantially radial direction of the cylindrical interior face of the connecting sliding piece and the first hole has an axis that is substantially radial relative to the cylindrical interior face of the connecting sliding piece so that the point and the anchoring screw converge toward the vertebra.

In one advantageous embodiment, facilitating the operations of assembling the components of the device after fixing the anchoring members to the vertebral column, the connecting sliding piece comprises:

a transverse exterior groove, a cylindrical bearing surface forming a first edge of the transverse groove opposite the first hole and conformed to receive a portion of the fastening rod, a clamping hole separate from the first hole in the bottom of the transverse groove separated from the first edge of the transverse groove by a distance greater than the diameter of the fastening rod, an oblique bearing surface constituting the second edge of the transverse groove and inclined to the axis of the clamping hole.

BRIEF DESCRIPTION OF THE DRAWINGS

Further subject matter, features and advantages of the present invention will emerge from the following description of particular embodiments of the invention, given with reference to the appended drawings, in which.

DESCRIPTION OF PREFERRED EMBODIMENTS

Figure 6:
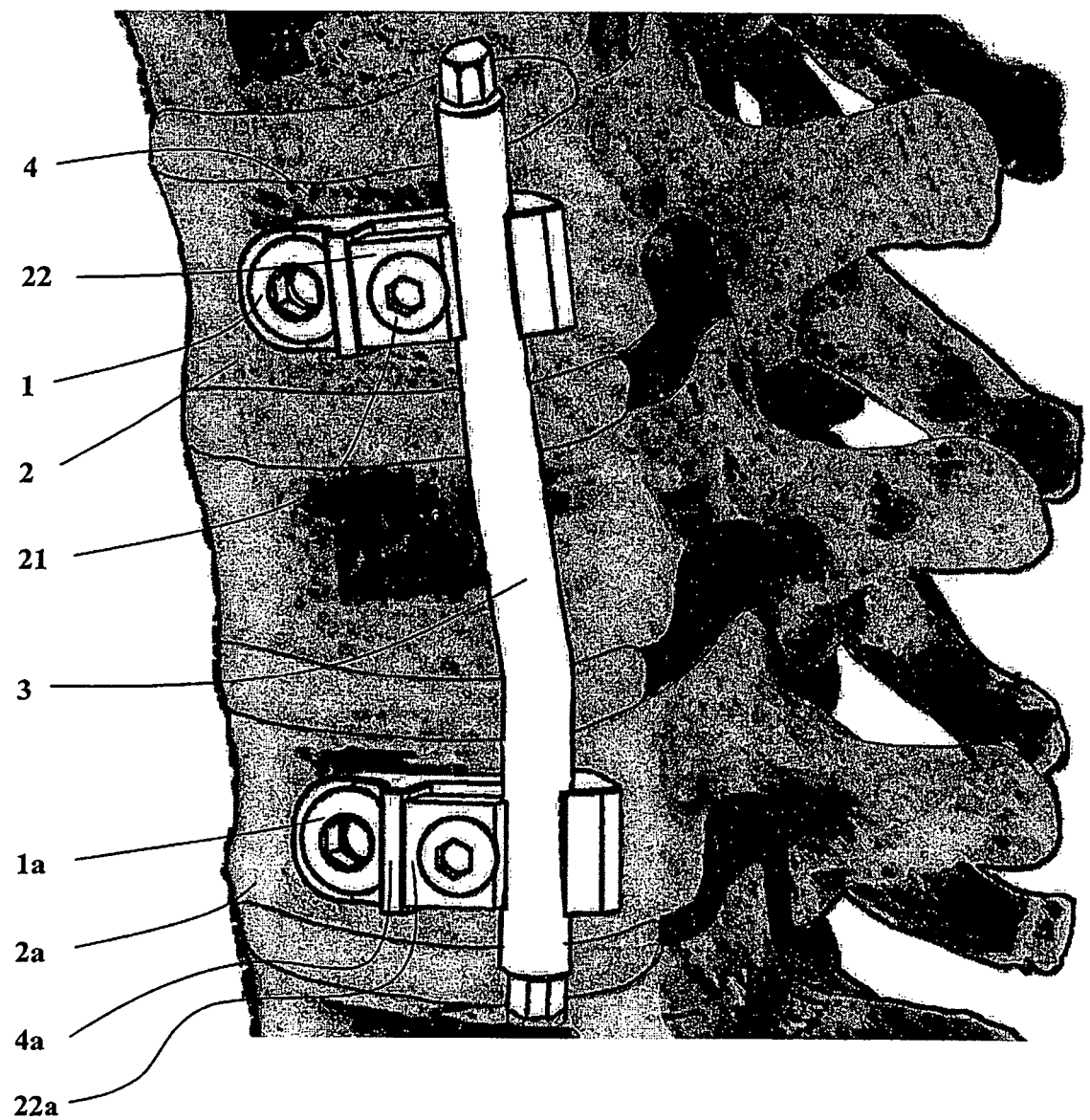
FIG. 6 shows the implantation of the supporting device of the invention on a vertebral column.

Consider first FIG. 6, which shows a device of the invention for supporting the vertebral column when fitted to a vertebral column.

The device of the invention for supporting the vertebral column comprises at least one connecting sliding piece 4 that connects an anchoring screw 1 to a fastening rod 3. The connecting sliding piece 4 is fixed to a vertebra 2 by the anchoring screw 1. Similarly, a second connecting sliding piece 4a is fixed to a second vertebra 2a by a second anchoring screw 1a. The fastening rod 3 is fixed to both connecting sliding pieces 4 and 4a so that the device provides a mechanical connection between the two vertebrae 2 and 2a.

Refer now to FIGS. 1 to 5, which show the connecting sliding piece 4 and the anchoring screw 1.

The anchoring screw 1 comprises a threaded shank 5 conformed to be screwed into the bone of a vertebra and a head 6 with a hexagonal axial hole 7 adapted to have a screwing tool inserted into it.

The structure of the connecting sliding piece 4 is elongate in a general lengthwise direction III, delimited by an interior face 11 adapted to bear against a vertebra, and delimited by an exterior face 13. The connecting sliding piece 4 comprises a first hole 16 conformed to have the shank 5 of the anchoring screw 1 passed through it in a direction I generally perpendicular to the interior face 11 and the exterior face 13. On being screwed into the bone of a vertebra, the anchoring screw 1 is fixed to the connecting sliding piece 4 by virtue of the fact that its head 6 comes to bear on the exterior face 13 of the connecting sliding piece 4, around the first hole 16.

The connecting sliding piece 4 comprises receiving means, for example a transverse cylindrical bearing surface 18 opening onto the exterior face 13, for receiving a portion of the fastening rod 3, and clamping means, such as a jumper 22 and a tightening screw 21, for clamping the fastening rod 3 into said transverse cylindrical bearing surface 18 of the receiving means or releasing it therefrom. In the assembled position, as shown in FIG. 6, the fastening rod 3 is therefore oriented along a transverse axis IV (FIG. 2) perpendicular to the general lengthwise direction III (FIG. 1) of the connecting sliding piece 4.

According to the invention, the connecting sliding piece 4 comprises at least one point 9 conformed to penetrate into the bone of a vertebra and thus to retain the connecting sliding piece 4 on the vertebra.

In the embodiment shown in the figures, the connecting sliding piece 4 comprises two parallel points 9 and 10 offset from each other in the direction of the transverse axis IV (FIG. 2) of the connecting sliding piece 4, parallel to the fastening rod. The points 9 and 10 are disposed in the portion of the sliding piece comprising the transverse cylindrical bearing surface 18 forming receiving means on the interior face 11 of the connecting sliding piece 4, opposite the receiving means on the exterior face 13.

Each point 9 or 10 shown here is a flat, generally triangular structure lying in a plane perpendicular to the direction of the transverse axis IV. Each point 9 and 10 preferably comprises retaining teeth, such as the teeth 9a and 9b on the two edges of the triangle.

The interior face 11 of the sliding piece 4, which is the face intended to bear against the vertebra, is concave and substantially cylindrical with a circular profile in the lengthwise plane of the connecting sliding piece 4 containing the axes I and III. The radius of the cylindrical portion can advantageously be from approximately 25 millimeters to approximately 35 millimeters to conform to the anatomical curvature of the anterolateral face of a vertebra.

Figure 1:
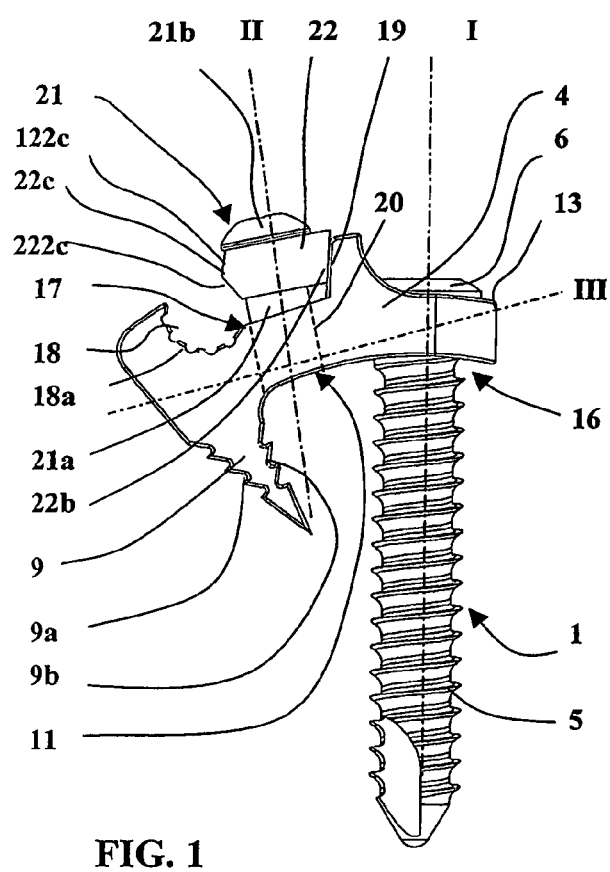
FIG. 1 is a front view of one embodiment of a device according to the present invention for supporting the vertebral column.
Figure 2:
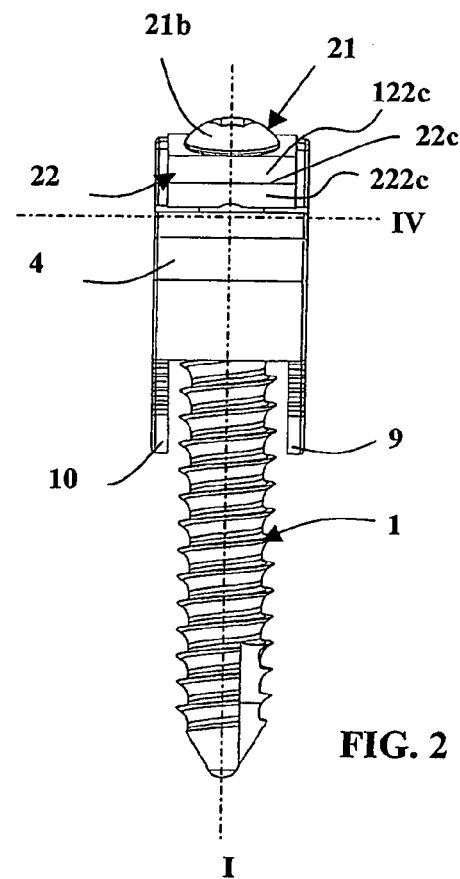
FIG. 2 is a left-hand side view of the FIG. 1 device.
Figure 3:
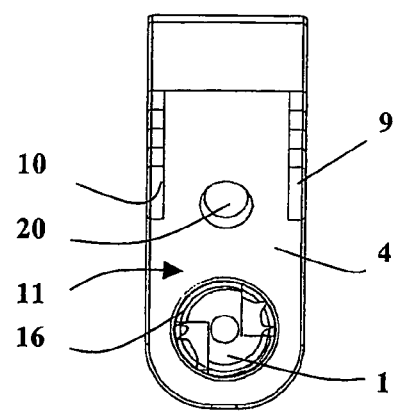
FIG. 3 is a bottom view of the FIG. 1 device.

In FIG. 1, each point 9 and 10 extends in a substantially radial direction of the cylindrical interior face 11 of the connecting sliding piece 4 and the first hole 16 has an axis I that is substantially radial relative to the cylindrical interior face 11 of the connecting sliding piece 4. As a result, the points 9 and 10 and the anchoring screw 1 converge toward the vertebra and oppose pulling out. The anti-pulling out effect is enhanced by making the length of the points approximately equal to the distance between their base and the first hole 16.

The connecting sliding piece 4 comprises the first hole 16 conformed to have the shank 5 of the anchoring screw 1 passed through it and on its exterior face 13 an exterior transverse groove 17 conformed both to receive the portion of the fastening rod 3 and to contain clamping means for selectively clamping the fastening rod 3 into the transverse groove 17 and releasing it therefrom.

Figure 4:
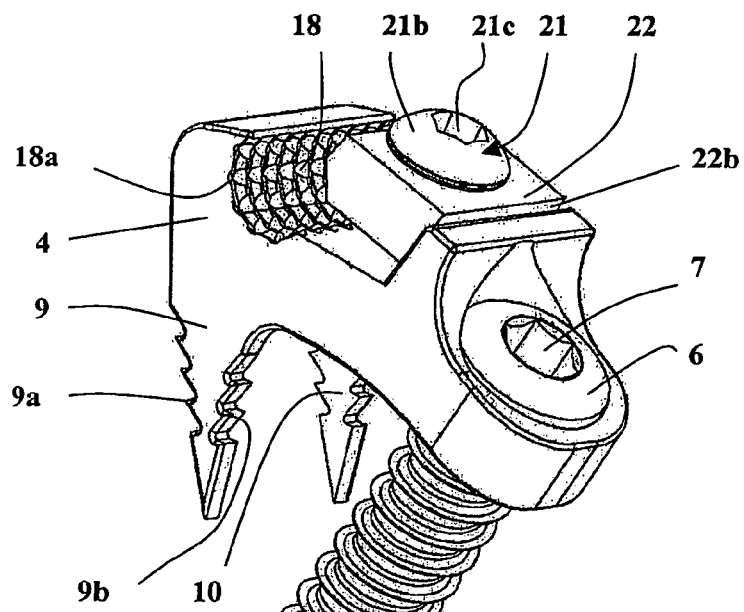
FIG. 4 is a perspective view of the FIG. 1 device.
Figure 5:
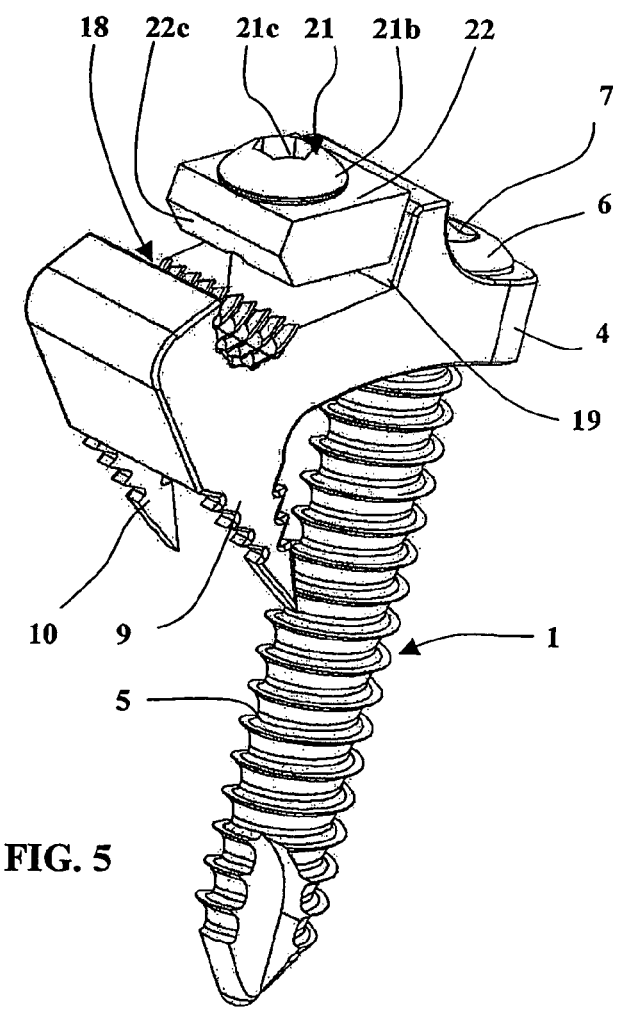
FIG. 5 is another perspective view of the FIG. 1 device.

The transverse groove 17 comprises the cylindrical bearing surface 18, which constitutes its first edge and is conformed to receive the portion of the fastening rod 3, surrounding it over an angle of approximately 120°, for example, as shown in FIGS. 1, 4 and 5. The cylindrical bearing surface 18 preferably includes anti-slip raised portions 18a that effectively oppose any displacement of the fastening rod 3 in the connecting piece 4 after clamping, either in translation or in rotation.

The second edge of the transverse groove 17 consists of an oblique bearing surface 19 that is inclined so that the transverse groove 17 is flared in the outward direction.

The connecting sliding piece 4 includes a threaded clamping hole 20 separate from the first hole 16 in the bottom of the transverse groove 17 of the connecting sliding piece 4. To provide a passage for said fastening rod 3, the clamping hole 20 is at a distance from the first edge of the transverse groove 17 greater than the diameter of the fastening rod 3.

A tightening screw 21 having a threaded shank 21a and a head 21b is screwed into the clamping hole 20.

The clamping hole 20 is offset toward the points 9 and 10 relative to the first hole 16 in the general lengthwise direction III and its axis II is preferably slightly oblique to the axis I of the first hole 16, the axes I and II defining an angle whose apex is directed inward, i.e. away from the transverse groove 17. Thus the clamping hole 20 is obliquely oriented relative to the axis I of the first hole 16 in the direction in which the first hole 16 moves toward the axis I when the tightening screw 21 is tightened.

The oblique bearing surface 19 that delimits the second edge of the transverse groove 17 is inclined and defines with the axis II of the clamping hole 20 an angle whose apex is also directed inward.

A jumper 22 is engaged in the manner of a wedge in the transverse groove 17 between the oblique bearing surface 19 and the fastening rod 3. The jumper 22 is pushed toward the bottom of the transverse groove 17 by the tightening screw 21. To this end, the jumper 22 is pierced by a jumper hole 22a through which the shank 21a of the tightening screw 21 is passed so that the head 21b of the tightening screw 21 bears on the external face of the jumper 22 and pushes it toward the bottom of the transverse groove 17.

The jumper 22 preferably turns freely about the tightening screw 21 and is preferably retained axially on the threaded shank 21a of the tightening screw 21 by a flange on the tightening screw 21 that engages in an oval annular groove on the interior face of the jumper hole 22a.

The jumper 22 has a bearing face 22b that is in sliding bearing engagement with the oblique bearing surface 19 of the connecting sliding piece 4 and has a thrust face 22c on the opposite side bearing on the fastening rod 3 to immobilize it in the transverse groove 17. The thrust face 22c (FIGS. 1 and 2) advantageously has a lower portion 222c, which may be plane and is generally obliquely oriented toward the bottom of the transverse groove 17 to bear against an upper portion of the fastening rod 3, and an upper portion 122c that is open upward and obliquely to facilitate lateral engagement of the fastening rod 3.

In a preferred embodiment, the head 21b of the tightening screw 21 comprises a polygonal contour axial hole 21c adapted to have a screwing tool inserted into it and the external face of the head 21b has a spherical dome shape.

The height of a structure of the above kind with a connecting sliding piece 4, a jumper 22 and a tightening screw 21 is particularly low, which considerably reduces the bulk of the device and consequently reduces the problems occasioned by fitting the device to a vertebral column.

In the preferred embodiment shown in the figures, in end position the fastening rod 3 is engaged in the transverse groove 17 on the opposite side of the anchoring screw 1 to the tightening screw 21. As a result of this, when the device of the invention is fitted to a vertebral column, as shown in FIG. 6, the fastening rod 3 is closer to the rear of the vertebral column, enabling it to be placed in the best position for absorbing mechanical forces between the successive vertebrae 2 and 2a. This also facilitates access to the tightening screws, such as the screw 21, which are positioned closer to the front of the vertebral column.

The device of the invention allows the use of a fastening rod 3 or a plurality of fastening rod elements with curvatures appropriate to the vertebral region to be treated.

The connecting sliding pieces 4 or 4a are easily fitted to the vertebrae 2 or 2a since each can initially be applied forcibly to a vertebra 2 or 2a, causing the points 9 and 10 to penetrate the bone, and then fastened more effectively to the vertebra 2 or 2a by screwing in the anchoring screw 1. The fastening rod 3 may then be engaged laterally, sliding and pivoting freely on the connecting sliding piece 4 regardless of its curvature, after which the fastening rod 3 is fixed to the connecting sliding piece 4 by tightening the tightening screw 21.

The deformed vertebral column reduction principle is three-dimensional. It is necessary to transform a scoliotic curvature oriented in a plane close to the frontal plane into a physiological curve situated in the sagittal plane and having a normal cyphotic, thoracic and lordotic curvature.

The fastening rod 3 is first given a shape close to the normal physiological curvature and is positioned on the patient, fixing its two ends by correctly tightening the anchoring members 1, 1a, the connecting sliding pieces 4 and 4a and the jumpers 22, 22a. The anti-slip raised portions 18a of the connecting sliding pieces 4 and 4a ensure highly effective immobilization of the fastening rod 3, in translation and most importantly in rotation. Anchoring members and sliding connecting pieces are then fitted on or in the other intermediate vertebrae, the fastening rod 3 is engaged in the intermediate connecting sliding pieces, and the fastening rod 3 is then locked by tightening the tightening screws of the intermediate connecting sliding pieces.

The device of the invention may be fitted in a much shorter operating time than the prior art devices, given the increased ease with which the surgeon can offer up and assemble the components of the device to each other and to the vertebral column during anterolateral implantation. The stability of the device is also significantly improved, enabling absorption of greater mechanical forces between the successive vertebrae, since, in the anterior position, the anchoring screw 1 is able to penetrate into a region of the vertebra in which the bone is generally stronger, whilst at the same time, in the posterior position, the fastening rod 3 is better placed to support the vertebral column.

The present invention is not limited to the embodiments that have been described explicitly and encompasses variants and generalizations thereof that fall within the scope of the following claims.

The invention claimed is:

1. Device for vertebral column support, comprising at least one connecting sliding piece for connecting an anchoring screw to a fastening rod, the structure of the connecting sliding piece being elongate in a general lengthwise direction, the connecting sliding piece comprising a first hole conformed for the passage and fixing of the anchoring screw, the connecting sliding piece comprising receiving means adapted to receive a portion of the fastening rod oriented along a transverse axis perpendicular to the lengthwise direction and to receive clamping means for selectively clamping the fastening rod in said receiving means or releasing it therefrom, wherein:

the connecting sliding piece comprises two points conformed to penetrate into the bone of a vertebra to retain the connecting sliding piece on the vertebra, the two points are disposed in the region of the sliding piece including the receiving means, on the interior face of the sliding piece and opposite the receiving means, which are on the exterior face of the connecting sliding piece, the two points are parallel to and offset from each other in the direction of the transverse axis of the connecting sliding piece, parallel to the fastening rod, the fastening rod is engaged in the end of the receiving means opposite the anchoring screw in the general lengthwise direction, wherein the connecting sliding piece comprises:

a transverse exterior groove, a cylindrical bearing surface forming a first edge of the transverse groove opposite the first hole and conformed to receive a portion of the fastening rod, a clamping hole separate from the first hole in the bottom of the transverse groove separated from the first edge of the transverse groove by a distance greater than the diameter of the fastening rod, an oblique bearing surface constituting the second edge of the transverse groove and inclined to the axis of the clamping hole, wherein the clamping means comprise:

a tightening screw with a head and a threaded shank adapted to be screwed into the clamping hole, a jumper adapted to be engaged in the manner of a wedge in the transverse groove between the oblique bearing surface and the fastening rod and adapted to be pushed toward the bottom of the transverse groove by the tightening screw with a bearing face in sliding bearing engagement with the oblique portion and with an opposite thrust face bearing on the fastening rod.

2. Device according to claim 1, wherein the jumper is pierced by a jumper hole through which is passed the shank of the tightening screw whose head bears on the external face of the jumper to push it toward the bottom of the transverse groove.

3. Device according to claim 1, wherein the head of the tightening screw includes a polygonal contour axial hole for turning it.

4. Device according to claim 1, wherein the thrust face of the jumper has a lower portion oriented generally toward the bottom of the transverse groove to bear against the fastening rod and an upper portion open upward to facilitate lateral engagement of the fastening rod.

* * * * *